Figure 1:
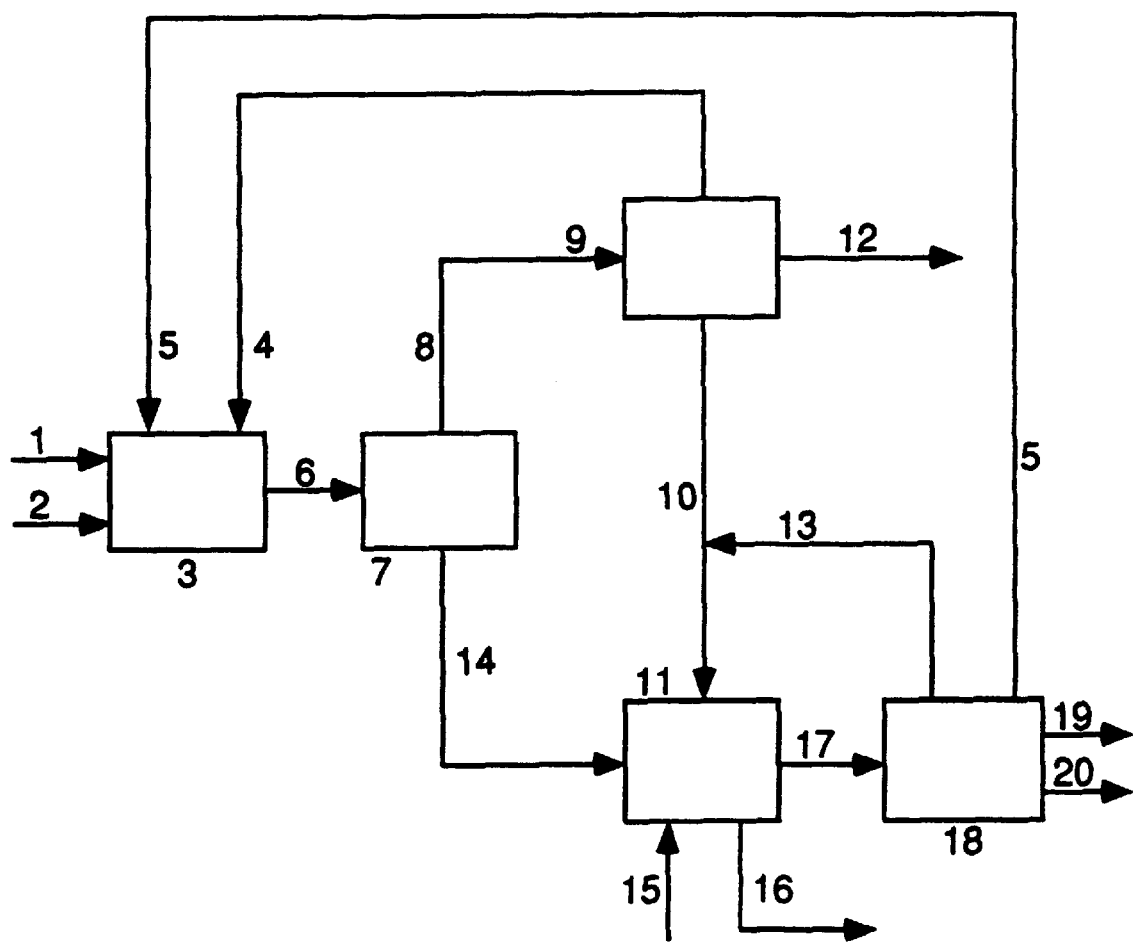

United States Patent [19]
Kratz et al.

[11] Patent Number: 6,018,074
[45] Date of Patent: Jan. 25, 2000

[54] PROCESS FOR THE PREPARATION OF POLYALCOHOLS

[75] Inventors: Detlef Kratz, Heidelberg; Achim Stammer, Freinsheim; Tom Witzel, Ludwigshafen; Martin Brudermüller, Mannheim, all of Germany

[73] Assignee: BASF Aktiengesellshcaft, Ludwigshafen, Germany

[21] Appl. No.: 09/068,300

[22] PCT Filed: Nov. 11, 1996

[86] PCT No.: PCT/EP96/04922

§ 371 Date: Oct. 5, 1998

§ 102(e) Date: Oct. 5, 1998

[87] PCT Pub. No.: WO97/17313

PCT Pub. Date: May 15, 1997

[30] Foreign Application Priority Data

Nov. 10, 1995 [DE] Germany ............ 195 42 036

[51] Int. Cl.[7] ............ C07C 45/00; C07C 31/18
[52] U.S. Cl. ............ 560/234; 568/854; 568/464; 568/853; 560/234; 560/238
[58] Field of Search ............ 568/853, 854, 568/464; 560/234

[56] References Cited

U.S. PATENT DOCUMENTS

| | | | |
|---|---|---|---|
| 2,292,926 | 8/1942 | Brubaker et al. | 568/853 |
| 2,790,837 | 4/1957 | Robeson | 568/853 |
| 3,097,245 | 7/1963 | Russell et al. | 568/853 |
| 3,478,115 | 11/1969 | Bronstein et al. | 568/853 |
| 3,876,706 | 4/1975 | Levanevsky et al. | 568/464 |
| 4,247,485 | 1/1981 | Immel et al. | 568/464 |
| 4,283,565 | 8/1981 | Bernhardt et al. | 568/648 |
| 4,301,310 | 11/1981 | Wagner | 568/863 |
| 4,594,461 | 6/1986 | Merger et al. | 568/853 |
| 5,149,861 | 9/1992 | Merger et al. | 560/234 |

FOREIGN PATENT DOCUMENTS 1535826  12/1978  United Kingdom.
94/07831  4/1994  WIPO.

OTHER PUBLICATIONS

Nurberdiev et al., *J. of General Chemistry of the USSR*, vol. 57, No. 7, part 2, pp. 1411–1413, 1987.

*Primary Examiner*—Paul J. Killos
*Assistant Examiner*—Taylor V. Oh
*Attorney, Agent, or Firm*—Keil & Weinkauf

[57] ABSTRACT

A process for the preparation of polyalcohols comprises the stages:

(a) Reaction of an alkanal or ketone with formaldehyde in aqueous solution in the presence of a tertiary amine, to form a formates containing polyalcohol product mixture, (b) removal of water, excess tertiary amine, excess formaldehyde (c) heating of remaining mixture from (b) with removal of further formaldehyde and tertiary amine with formation of the formates of the polyalcohol, (d) transfer of tertiary amine removed from stage (b) and/or from stage (c), to synthesis stage (a) and/or to the subsequent transesterification stage (e), (e) transesterification of the resulting formates of the polyalcohol from stage (c) with an alcohol of the formula ROH in the presence of a transesterification catalyst to give polyalcohols and formates of the formula

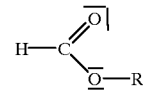

where R is a hydrocarbon radical, preferably alkyl of 1–6, particularly preferably 1–2, carbon atoms, and (f) isolation of the polyalcohols.

14 Claims, 2 Drawing Sheets

PROCESS FOR THE PREPARATION OF POLYALCOHOLS

The present invention relates to a process for the preparation of polyalcohols, ie. polymethylolalkanes and polymethylolcycloalkanes, by reacting alkanes or ketones (which include cyclic ketones) with formaldehyde in the presence of a tertiary amine.

It is known that alkanals can be reacted with excess amounts of formaldehyde with the addition of stoichiometric amounts of an inorganic base (eg. sodium hydroxide solution, calcium hydroxide solution, calcium oxide or barium hydroxide) in aqueous solution to give di-, tri- and in the case of acetaldehyde tetramethylolalkanes. The reaction takes place in a plurality of steps. After one or two, in the case of acetaldehyde three aldol reactions of formaldehyde and the alkanal to give the corresponding mono-, di- and in the case of acetaldehyde trimethylolalkanal, the polyalcohol and an alkali metal formate or alkaline earth metal formate are formed in a crossed Cannizzaro reaction with formaldehyde under the action of the inorganic base.

The amounts of inorganic formate obtained in this procedure interfere with the isolation of the polyalcohol and must be quantitatively separated off before the purification. A plurality of methods is available for the separation, among which the extraction of the polyalcohol, electrodialysis or precipitation of the inorganic salt by a change of solvent are the commonest. A disadvantage is the high cost of these processes; in addition, an aqueous residue of the inorganic salt, contaminated with the extracting agent, remains behind and leads to considerable environmental pollution.

Various other processes for solving this problem in the preparation of polyalcohols have been suggested.

German Laid-Open Application DOS 2,507,461 describes a process for the preparation of 2,2-dimethylolalkanals. These are obtained by reacting aldehydes of the formula

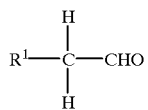

where $R^1$ is an aliphatic radical, with formaldehyde in the presence of tertiary branched alkylamines. The 2,2-dimethylolalkanals prepared by this process are useful intermediates for the preparation of trimethylolalkanes via hydrogenation.

A camizzaro reaction shall be a voided. For example, the reaction of n-butyraldehyde with formaldehyde under the catalytic action of a branched tertiary amine gives dimethylolbutanal. This is distilled and can then be hydrogenated to trimethylolpropane (TMP), although the yields obtained here are unsatisfactory.

German Laid-Open Application DOS 2,813,201 describes also a process for the preparation of 2,2-dimethylolalkanals, aldehydes being reacted with formaldehyde in a molar ratio of 1:5–1:30 in the presence of hydroxides and/or carbonates of the alkali metals and/or alkaline earth metals and/or tertiary amines. A hydrogenation to form trimethylolalkanes may follow. Before the reduction to the trimethylolalkane, any amine used, the formaldehyde used in excess and unconverted aldehyde should be separated off. A high excess of formaldehyde is required for obtaining high yields.

This process is not very suitable for an industrial preparation of trimethylolpropane, since the large excess of formaldehyde has to be separated off before the catalytic hydrogenation. In the reaction formic acid formed is fixed as a trialkyl ammonium formiate and removed by distillation. The distillation is difficult to carry out in industrial scale it very pure products are desired.

EP-A-0 142 090 discloses a process for the preparation of trimethylolalkanes by reaction of 1 mol of an n-alkanal with 2.2–4.5 mol of formaldehyde and 0.6–3 mol of a trialkylamine in aqueous solution and subsequent hydrogenation. Here, the reaction mixture is worked up by distillation before or after the hydrogenation.

EP-A-0 289 921 describes a process in which the synthesis mixture is hydrogenated in the same manner as in the process described in EP-A-0 142 090. In the embodiment (a) of the process described in EP-A-0 289 921, in the preparation of trimethylolalkanes by reaction of n-alkanals with 2.2–4.5 mol of formaldehyde in aqueous solution in the presence of 0.6–3 mol of a trialkylamine, based in each case on 1 mol of alkanal, and subsequent hydrogenation, the crude reaction mixture is heated to 100–200° C., the water present in the reaction mixture being substantially separated off by distillation, together with any excess, free trialkylamine, and the trialkylammonium formate being reacted with the trimethylolalkane under formation of trimethylolalkane formiate of the trialkylamine being distilled off and the trimethylolalkane formate being esterified with methanol in the presence or absence of catalytic amounts of alkali metal or alkaline earth metal alcoholates to give trimethylolalkane and methyl formate. The methyl formate is removed.

A disadvantage of this process is that hydrogenation of the crude synthesis mixture is required for obtaining high yields and the formaldehyde used in excess is lost during the hydrogenation in the form of methanol, and the industrial implementation of the process is thus considerably limited.

In the variant (b) of the process described in EP-A-289 921, the synthesis mixture is substantially dewatered after catalytic hydrogenation, any excess free trialkylamine being separated off.

The trialkylamine present in the form of trialkylammonium formate is liberated by adding methanol to the remaining mixture and heating to 100–200° C. with formation of methyl formate and trialkylamine. The reaction products are isolated in a manner known per se.

As in process variant (a), in process variant (b) too a hydrogenation of the discharged synthesis mixture is required for achieving satisfactory yields, resulting in the loss of the excess formaldehyde.

The processes described so far relate only to the preparation of dimethylolalkanes and/or trimethylolalkanes.

However, a process which also permits the preparation of tetramethylolalkanes, tetramethylolcycloalkanes and higher polymethylolalkanes and polymethylolcycloalkanes, in which equimolar amounts of organic formate salt are not formed, is desirable, which can be carried out economically in few steps.

It is an object of the present invention to provide a process for the preparation of polyalcohols, which comprise polymethylolalkanes and polymethylolcycloalkanes.

The process should permit the preparation of very pure polyalcohols in a simple manner and efficiently from the economic point of view. A further object of the invention is to achieve a high yield. According to the invention, it is also intended to provide a process for the preparation of polyalcohols which manages with very few stages and without hydrogenation, produces little waste product, especially alkali formiates, and uses starting materials preferably in a plurality of stages.

We have found that this object is achieved and that, according to a first embodiment of the invention, a process for the preparation of a polyalcohol product, is provided. In this process, an alkanal or ketone is reacted with formaldehyde in aqueous solution in the presence of a tertiary amine, this reaction being effected, according to the invention, with use of a temperature gradient. The reaction is carried out using a temperature gradient with increasing temperature, preferably using a two- or three-stage temperature gradient. The reaction using a temperature gradient is particularly preferably carried out in a temperature range of 20–90° C. for 0.5–24, in particular 1–6, hours. Temperature gradient means the sequential stepwise reaction on different temperature levels, wherein the temperature increases from step to step. The reaction is thus carried out in subsequent steps of in increasing temperature. The reaction hads polyalcohol products in high yields.

A further embodiment of the invention is the preparation of polyalcohols by transesterification. In this process, the formate of a polyalcohol is subjected to transesterification with a low-boiling alcohol of the formula ROH in the presence of a tertiary amine, preferably a trialkylamine, as a transesterification catalyst to give a polyalcohol and a formate of the formula

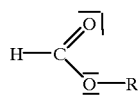

where R is a hydrocarbon radical, preferably alkyl of 1 to 6, preferably 1 or 2, carbon atoms.

We have found that the above object is furthermore achieved by an overall process for the preparation of polyalcohols, as defined in the claims. This process comprises the following stages:

(a) Reaction of an alkanal or ketone with formaldehyde in aqueous solution in the presence of a tertiary amine, to form a formates containing polyalcohol product mixture, (b) removal of water, excess tertiary amine, excess formaldehyde (c) heating of remaining mixture from (b) with removal of further formaldehyde and tertiary amine with formation of the formates of the polyalcohol, (d) transfer of tertiary amine removed from stage (b) and/or from stage (c), to synthesis stage (a) and/or to the subsequent transesterification stage (e), (e) transesterification of the resulting formates of the polyalcohol from stage (c) with an alcohol of the formula ROH in the presence of a transesterification catalyst to give polyalcohols and formates of the formula

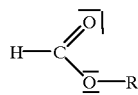

where R is a hydrocarbon radical, preferably alkyl of 1–6, particularly preferably 1–2, carbon atoms, and (f) isolation of the polyalcohols.

The tertiary amine is returned to the reaction which increases the effectiveness of the process. All products removed in steps (b) and (c) can be returned, optionally after seperation from low and medium boilers.

The reaction of alkanal or ketone with formaldehyde in the presence of a tertiary amine is carried out batchwise or continuously. The continuous procedure is preferred. The product mixture of stage (a) contains mainly polyalcohol, polyalcohol semi formales, polyalcohol formates already formed, and trialkyl ammonium formate. Because of the extensive reaction to form polyalcohols no hydrogenation is necessary.

In stage (a), methanol can be formed from formaldehyde by Cannizzaro reaction to formic acid and methanol. This is preferably separated from the remaining reaction mixture, together with water, excess tertiary amine and excess formaldehyde. This separation is effected in particular by means of distillation.

The process according to the invention is preferably carried out in such a way that polyalcohols are prepared without hydrogenation.

Furthermore, in a particular variant of the novel process, tertiary amine, water and unconverted formaldehyde are circulated and the process is thus made very efficient from the economic point of view.

In one variant of the process, the transesterification of the formates with a low-boiling alcohol is carried out in the presence of a tertiary amine, it being possible in particular to use, as the tertiary amine, the same amine as in the synthesis stage.

The preparation of the crude synthesis mixture (stage (a), for example preparation of the methylol product) is carried out batchwise or continuously, preferably continuously, under reduced, superatmospheric or atmospheric pressure, preferably atmospheric pressure. The reaction is carried out in general at up to 200° C., preferably 10–120° C., in particular 30–80° C. In the continuous procedure, for example, a reactor cascade comprising from two to five, preferably three, stirred kettles connected in series is used, and said kettles may be at different temperatures as a result of cooling or heating. The temperatures of the individual kettles are from 10 to 150° C.

Surprisingly, higher yields of crude polyalcohols are obtained and the formation of byproducts (for example dimeric ethers of polyalcohol, formaldehyde bis (polyalcohol)acetals, cyclic acetals of the polyalcohol and dehydration products) is considerably reduced by temperature gradation T (kettle n)>T (kettle n−1), where n is preferably 2–4, for example in a three-stage reactor cascade having a temperature gradient of 20–40° C./40–70° C./70–90° C., preferably about 40° C./60° C./80° C. Excess formaldehyde presents no problem and is present in bonded form as a hemiformal in reversible equilibrium on the alcohol functions of the polyalcohol.

Advantageously, dimeric polyalcohol ethers formed in the novel process, and any other higher or modified polyalcohol products, can be obtained as useful products. This advantage is achieved by virtue of the fact that the tertiary amine is used for the reaction or transesterification instead of, for example, sodium hydroxide. The use of such catalysts result in the formation of salts, so that the abovementioned useful products in any case cannot be obtained economically.

The reaction time may be from 0.5 to 24, preferably from 1 to 6, hours.

Formaldehyde is used in the usual industrial form as a 10–50% strength aqueous solution, and the water content of the reaction mixture is from 40 to 85%, preferably from 60 to 75%, in particular 68%.

The alkanals used are preferably those of 2–12, in particular 2–8, carbon atoms. Examples of particularly suitable alkanals are acetaldehyde, n-propanal, n-butanal, n-pentanal, 3-methylbutanal, n-hexanal, 3-methylpentanal, 2-ethylhexanal and n-heptanal.

Preferably used ketones are aliphatic ketones, preferably those of 3–18, in particular 3–8, carbon atoms. Cyclic ketones of 4–8, in particular 6, carbon atoms are preferred. Cyclohexanone is particularly preferably used. The aldehyde or keto function may also be present repeatedly in the molecule.

Examples of tertiary amines are the amines mentioned in German Laid-Open Application DOS 2,507,461.

Particularly advantageously used tertiary amines are tri-n-alkylamines, such as trimethylamine, triethylamine, tri-n-propylamine or tri-n-butylamine.

The preferred molar ratio of the reactants (alkanal or ketone/formaldehyde/tertiary amine) is 1/0.5–10/0.6–5, preferably 1/2.5–6/0.8–2, in particular about 1/4.5/1.5.

The dewatering of the reaction mixture (steps (b), (c) and the simultaneous removal of the low boilers, ie. excess tertiary amine (for example trialkylamine), excess formaldehyde and the methanol formed from the Cannizzaro reaction of formaldehyde, can be carried out in one or more stages in a conventional apparatus suitable for distillation. For example, a rotary evaporator is suitable for the batchwise procedure and a falling-film evaporator for the continuous procedure. The separation may be carried out under reduced or atmospheric pressure or in the presence of an inert gas stream; the separation is preferably effected to a residual water content of 2–30% by weight, based on the reaction solution. The reaction solution contains, as principal components, the polyalcohol, polyalcohol hemiformals, already formed formates of the polyalcohol and trialkylammonium formates.

The esterification to give formates of the polyalcohol (step (c)) takes place autocatalytically as a result of further distilling off of water (of reaction), tertiary amine and the formaldehyde liberated from the polyalcohol hemiformals previously formed. Thereby the amine is liberated from the formates of the tertiary amine. The reaction can be carried out batchwise but is preferably effected continuously, under atmospheric pressure or reduced pressure of from 0.1 to 760 mbar. The reaction temperature is from 70 to 250° C., preferably from 150 to 210° C. A bubble cap column having a forced-circulation evaporator is suitable for the continuous procedure. The feed takes place in the upper part of the column, and the residence time in the stripping section together with the forced-circulation evaporator is 0.5–5, preferably 2–3, hours. The formaldehyde liberated does not interfere with the course of the reaction by forming insoluble oligomeric formaldehyde deposits, since water of reaction is continuously formed by the esterification reaction and keeps the formaldehyde in solution.

The transesterification of the formates of the polyalcohol (step (e)) to, for example, alkyl formate and free polyalcohol can be carried out batchwise, for example in a stirred kettle, or continuously in the presence of 0.5–20, preferably 1–15, in particular 1–4, mol of an alcohol per mol of the formate of the polyalcohol. A countercurrent column in which the formate is metered into the middle section and an alcohol into the lower section is suitable for the preferred continuous procedure. In the stripping section of the column, alkyl formate is separated from the alcohol added, so that substantially pure alkyl formate is condensed at the top of the column. The reaction time is 0.25–5, preferably 0.5–3, hours. Alcohols, in particular alkanols, of 1–6 carbon atoms are preferred. Alcohols in which the difference between the boiling point of the alcohol and that of the corresponding formate is very large are particularly suitable. The pairs methanol/methyl formate and ethanol/ethyl formate are preferably used.

The transesterification can be carried out in the presence of the typical homogeneous or inhomogeneous transesterification catalysts. Suitable inhomogeneous catalysts are acidic or basic alkali metal or alkaline earth metal oxides, hydrotalcite and alumina. Acidic or basic ion exchangers may also be used. Suitable homogeneous catalysts are alkali metal or alkaline earth metal alcoholates. When inorganic alcoholates are used as catalyst, transesterification is followed by removal of the catalyst by neutralization or ion exchange, either producing a salt or resulting in additional complexity with regard to process engineering. When heterogeneous catalysts are used, the life of these catalysts should be taken into account and regeneration may be necessary.

It is surprising that the transesterification in the presence of a tertiary amine, in particular a trialkylamine, can be carried out with a good result. Consequently, the catalyst can easily be removed by distillation after the reaction and can be reused. This possibility exists in the case of catalysts based on alkali metals. Suitable trialkylamines are the amines used in the reaction stage, it being possible to use, for example, the same amine in the synthesis reaction as in the transesterification reaction. The amount of amine used comprises a few mol %, but may also be superstoichiometric. It is preferably 1–50 mol %, based on 1 mol of formate as 100 mol %. If necessary, the amine is recovered quantitatively by distillation. The transesterification catalyzed by a tertiary amine takes place extremely rapidly, so that the necessary quantitative conversion to alkyl formate and the desired polyalcohol is achieved without problems. An advantage over the use of conventional transesterification catalysts, for example the alcoholates of the alkali metals and alkaline earth metals, which are hydrolyzed by water, is that the reaction can be carried out in the presence of a tertiary amine, for example a trialkylamine, in anhydrous or dilute aqueous solutions.

The distillate from the removal of the low boilers or the mixture distilled off in the formation of the formates of the polyalcohol (steps (b), (c), (d) and comprising water, trialkylamine and formaldehyde can particularly advantageously be used for the transesterification (e), if necessary after prior concentration and removal of the formaldehyde. On the one hand, the amount of methanol contained in these mixtures is thus utilized for the formation of methyl formate and, on the other hand, methanol is removed from the mixtures in this manner by chemical reaction. Since alcohols may adversely affect the synthesis stage, methanol must be separated off before the trialkylamine/water/formaldehyde mixture is recycled to the synthesis stage. This is possible with the aid of the transesterification reaction described, but cannot be achieved by simple distillation without loss of trialkylamine.

An alcoholic solution of the desired polyalcohol is obtained from the transesterification stage (step (f)). By varying the amount of alcoholic solvent used, crystalline polyalcohols can be obtained directly by crystallization. The alcohol used as a solvent and the tertiary amine used as a catalyst can be recycled to the transesterification (e.g. steps (d) and (e)). In the case of readily distillable polyalcohols, it is also possible first to distil off the low-boiling alcohol and tertiary amine and then to recycle them. Thereafter, the polyalcohol can be obtained directly. Neutralization or complicated removal of the transesterification catalyst is therefore unnecessary.

Preferably the desired polyalcohol and a mixture of alcohol and tertiary amine are obtained in stage (f) by separation, preferably by distillation, and some of said mixture is recycled to stage (e), and a part of this mixture of alcohol and tertiary amine is transferred to a stage (g) in which materials isolated from stages (b) and (c) and this bleed stream from (f) are separated into the following three mixtures, the separation preferably being carried out by distillation:

1. an alcohol/tertiary amine mixture, at least some of which is fed to stage (e),
2. a water/tertiary amine/formaldehyde mixture, at least some of which is fed to stage (a), and
3. an aqueous solution enriched with medium boilers.

By way of example, two advantageous embodiments of the novel process for the preparation of polyalcohols from alkanals or ketones and formaldehyde under trialkylamine catalysis are illustrated schematically below with reference to the process diagrams in FIG. 1 and FIG. 2, such embodiments preferably being used, for example, in the preparation of 1,1,1-trimethylolpropane and formaldehyde or, for example, of pentaerythritol, from acetaldehyde and formaldehyde, in the presence of, for example, trimethylamine or triethylamine. For the sake of clarity, these embodiments are described below using only the reaction of alkanals with formaldehyde as an example.

Figure 2:
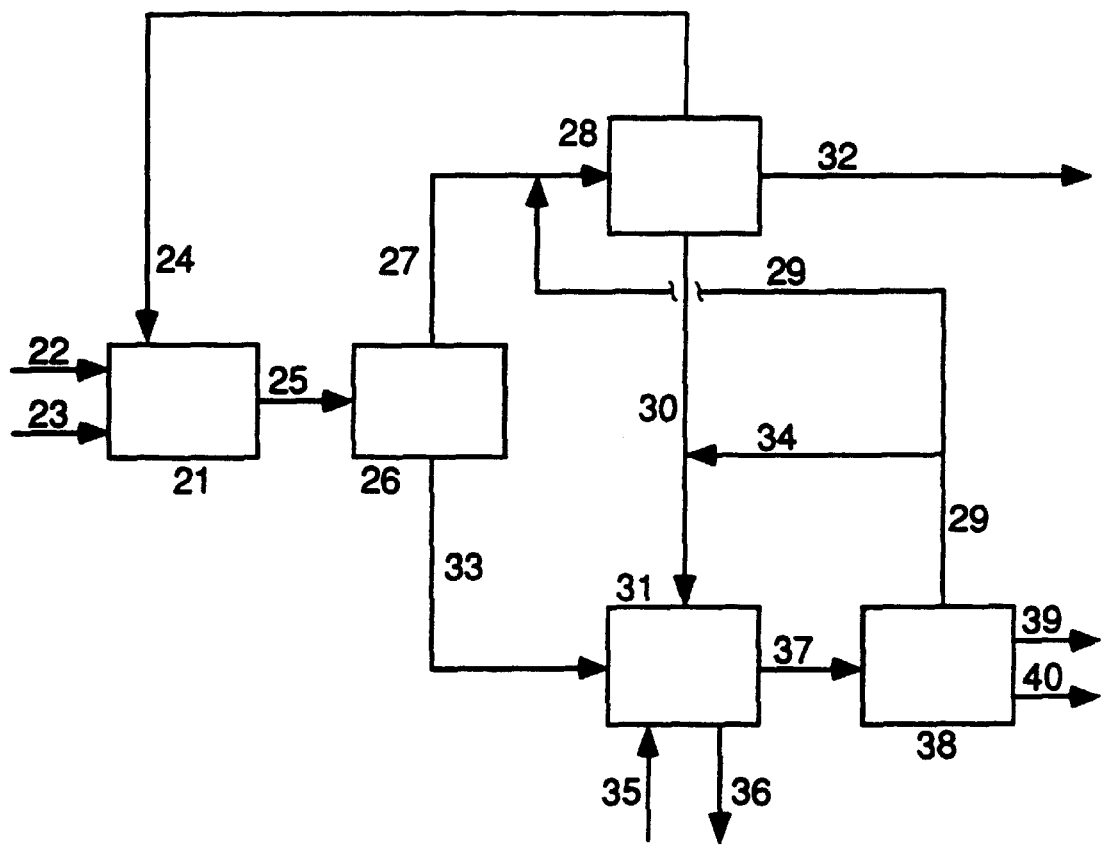

In the drawing FIGS. 1 and 2 show reaction schemes of the process according to the present invention.

In the process according to FIG. 1, formaldehyde and the relevant alkanals are passed via the lines 1 and 2, respectively, into the reactor 3, which is advantageously a stirred kettle cascade, and supplemented there with aqueous formaldehyde which is recycled via line 4 and may still contain small amounts of trialkylamine, and a recycled aqueous solution of the trialkylamine catalyst is added via line 5. The aldehyde which, depending on the starting material used, is bis- or trishydroxymethyl-substituted in the alpha position relative to the aldehyde group is formed in the reaction in reactor 3 and reacts, also in reactor 3, with further formaldehyde in a crossed Cannizzaro reaction to give the corresponding tris- or tetrahydroxymethyl compound—also referred to as trismethylol compound in this application (for the sake of clarity, only the term trimethylol compound is used below)—the formaldehyde being converted into formic acid and, in the presence of the trialkylamine catalyst, forming trialkylammonium formate salts. The discharge from reactor 3 is fed via line 6 to the middle section of a distillation column 7, which may advantageously be equipped with a forced-circulation evaporator in which low-boiling components of the discharge from reactor 3, such as water, formaldehyde, the trialkylamine, and methanol formed by the Cannizzaro reaction in reactor 3, are distilled off via the top, from the higher-boiling components of the discharge from reactor 3, such as the 1,1,1-trimethylolalkane and esters of trimethylolalkane with formic acid—the latter are formed in the distillation column by reaction of the trialkylammonium formate salt with the 1,1,1-trimethylolalkane, the trialkylamine catalyst being liberated again. Advantageously, the discharge from reactor 3 can be concentrated before being passed into the column 7, for example in a thin-film or falling-film evaporator not shown in FIG. 1.

The low-boiling components of the discharge from reactor 3 which are separated off in column 7 are fed via line 8 to a further column 9, where they are separated by distillation into three fractions, ie. a) a relatively low-boiling fraction which essentially consists of tri-alkylamine, methanol and water and is fed to the lower section of a further column 11 via line 10, if necessary after the addition of a recycled stream from line 13, containing further trialkylamine, water and methanol, b) a medium-boiling fraction which consists essentially of water and unconverted formaldehyde and may still contain small amounts of the trialkylamine and is recycled to the reactor 3 via line 4, and c) a high-boiling aqueous fraction which is enriched with byproducts, such as ethylacrolein and is removed from the process via line 12.

The high-boiling bottom product of column 7, which contains 1,1,1-trimethylolalkane and the ester of formic acid with the 1,1,1-trimethylolalkane, is pumped via line 14 into the middle section of column 11. Since the 1,1,1-trimethylolalkane and its ester with formic acid boil at a higher temperature than the mixture fed to the lower section of column 11 via line 10 or line 13 and comprising trialkylamine, methanol and water—the mixture from line 13 can be fed to column 11 via a separate inlet not shown in FIG. 1 or after being combined beforehand with the stream in line 10—and the methanol additionally introduced via line 15 into the lower section of column 11, the relatively high-boiling compound 1,1,1-trimethylolalkane and its ester with formic acid come into intimate contact, in column 11, with the lower-boiling components of the trialkylamine/methanol/water mixture passed into the lower section of the column, the ester of formic acid with the 1,1,1-trimethylolalkane undergoing complete transesterification with the methanol present in column 11 in excess relative to the formic ester, to give 1,1,1-trimethylolalkane and the very low-boiling methyl formate. The methyl formate is removed from the process at the top of column 11, via line 16, and is further used, for example for the preparation of formic acid or formamide.

The transesterification mixture of column 11, which has been freed from low-boiling methyl formate and essentially consists of the trialkylamine, excess methanol, water and the 1,1,1-trimethylolalkane, is taken off at the bottom of column 11 and passed via line 17 into the middle section of column 18, in which this mixture is separated into four fractions, ie. a) a relatively low-boiling mixture which essentially consists of trialkylamine, water and methanol and is taken off at the top of column 18 and recycled via line 13 to column 11, b) a mixture which consists essentially of trialkylamine and water and is removed from the upper part of the column and recycled via line 5 to reactor 3, c) a fraction which consists essentially of the 1,1,1-trimethylolalkane and is separated off in the lower section of column 18 and fed via line 19, for example to the tank farm, and d) a mixture which consists of high-boiling byproducts and is taken off at the bottom of column 18 and fed to a further distillation column not shown in FIG. 1, for the removal of the high boilers.

The cycle of the embodiment of the novel process according to FIG. 1 is thus complete. Losses of trialkylamine in the course of the process are replenished by feeding in fresh trialkylamine, preferably by adding it to reactor 3 via a feed not shown in FIG. 1.

In another advantageous embodiment of the novel process for the preparation of 1,1,1-trimethylolalkanes from alkylalkanals and formaldehyde, as shown schematically in FIG. 2, reactor 21 is fed with aqueous formaldehyde solution via line 22, with the alkanal via line 23 and with a recycled trialkylamine/formaldehyde/water mixture via line 24. If required, trialkylamine consumed in the course of the process can be replaced by fresh trialkylamine via a feed not shown in FIG. 2.

In the reaction in reactor 21, which is essentially the same as reactor 3 in FIG. 1, a product mixture having essentially the same composition as in reactor 3 is formed and is passed via line 25, if necessary after prior concentration, for example in a falling-film or thin-film evaporator, which is not shown, to the middle section of column 26, which practically corresponds to column 7 in FIG. 1, where the discharge from reactor 21 is esterified as described for the process relating to FIG. 1, and is separated into a lower-boiling fraction which consists essentially of trialkylamine, methanol, formaldehyde and water and is taken off at the top of column 26 and fed via line 27 to a further column 28 and into a higher-boiling bottom fraction consisting essentially of the 1,1,1-trimethylolalkane and its formic ester.

Before being passed into column 28, the mixture fed in line 27 to column 28 is advantageously combined with a mixture which is recycled via line 29 and composed essentially of trialkylamine and methanol, but which may alternatively also be fed into column 28 via a separate feed not shown in FIG. 2.

In contrast to the distillation procedure in column 9 in the embodiment according to FIG. 1, the mixture added to column 28 is separated into three fractions in such a way that a) a relatively low-boiling fraction which is composed essentially of trialkylamine and methanol and contains virtually no more water is taken off at the top of the column and is fed via line 30 to the lower section of a further column 31, b) a fraction which consists essentially of a mixture of the components trialkylamine, formaldehyde and water is cut in the upper part of column 28 and recycled via line 24 to the reactor 21, and c) a higher-boiling aqueous fraction enriched with byproducts, such as ethylacrolein, is removed from the process via line 32.

The high-boiling bottom product from column 26, consisting essentially of the 1,1,1-trimethylolalkane and its formic ester, is pumped via line 33 into the middle section of column 31. Since the 1,1,1-trimethylolalkane and its formic ester boil at a higher temperature than the mixture fed to the lower section of column 31 via line 30 or line 34 and comprising trialkylamine and methanol—the mixture from line 34 can be fed to column 31 via a separate feed, not shown in FIG. 2, or advantageously after prior combination with the stream in line 30—and the methanol additionally introduced into the lower section of column 31 via line 35, the relatively high-boiling compounds 1,1,1-trimethylolalkane and its formic ester come into intimate contact, in column 31, with the components of the lower-boiling trialkylamine/methanol mixture passed into the lower section of column 31, the ester of formic acid with the 1,1,1-trimethylolalkane undergoing virtually quantitative transesterification with the methanol present in column 31 in excess relative to the formic ester, to give 1,1,1-trimethylolalkane and the very low-boiling methyl formate. The methyl formate is removed from the process at the top of column 31 via line 36.

The transesterification mixture of column 31, which has been freed from the low-boiling methyl formate and is composed essentially of the trialkylamine, excess methanol and the 1,1,1-trimethylolalkane, is taken off at the bottom of column 31 and passed via line 37 into the middle section of column 38, in which this mixture is separated into three fractions, ie. a) a relatively low-boiling mixture which consists essentially of methanol and trialkylamine and is taken off at the top of column 38 and, after removal of a bleed-stream through line 34, recycled via lines 29 and 27 to column 28, b) a fraction which consists essentially of 1,1,1-trimethylolalkane and is separated off in the lower section of column 38 and fed via line 39, for example to the tank farm, and c) a mixture which consists of high-boiling byproducts and is removed from the process at the bottom of column 38 via line 40.

The bleed-stream containing methanol and trialkylamine and taken off from line 29 by means of line 34 is advantageously combined with the methanol/trialkylamine stream in line 30 and fed with this to column 31, in the manner described. The amount of the bleed-stream recycled via line 34 and 30 to the transesterification column is of course controlled so that a steady-state equilibrium is established in the plant, corresponding to the reaction and distillation conditions used and specified in the preceding part of the description.

EXAMPLE 1

32.1 ml of triethylamine (1.5 mol), 13.84 ml of n-butyraldehyde (1 mol) and 134.2 ml of formaldehyde (15% strength, 4.5 mol) are passed, per hour, into a continuously operated reactor cascade comprising three flasks connected in series and provided with stirrers (reaction volume in each case 300 ml). The stirred flasks are heated as follows: flask 1=42° C.; flask 2=60° C.; flask 3=78° C. The crude yield determined by GC analysis is 89% of TMP (trimethylolpropane), and the formic acid content is 5.2%.

Examples 2–9 in Table 1 were carried out similarly to Example 1, at the same temperatures but with different concentrations of the starting materials.

EXAMPLE 10

For separating off the low boilers and water, the crude discharge from Example 1 is pumped at room pressure into a falling-film evaporator which is heated at 150° C. The feed is 120 ml/h, the bottom discharge is 43 g/h and the amount of distillate is 80 g/h. The distillate has two phases; distillate composition: 87% of water, 8.5% of triethylamine, 3.5% of formaldehyde and 1% of methanol.

EXAMPLES 11 TO 14

The procedure is as in Example 10. The results are listed in Table 2.

EXAMPLE 15

A mixture of water (21%), formic acid (12%), triethylamine (27%), TMP (37%) and formaldehyde (1%) is pumped to the 8th tray of a 10-tray bubble cap column (V=300 ml) (feed 214 ml/h), which is operated at a top pressure of 63 mbar and a bottom temperature of 194° C. The bottom discharge is heated by means of a forced-circulation evaporator (reaction volume=150 ml), from which 100 g/h of TMP formates are pumped continuously. The condensate has two phases.

EXAMPLES 16 TO 18

The procedure is in principle as in Example 15. The modifications and results are listed in Table 3.

EXAMPLE 19

The bottom discharge from Example 10 (12.5% of water, 13.5% of formic acid, 35% of triethylamine, 30% of trimethylolpropane and trimethylolpropane hemiformals, 3% of dimeric TMP and 4% of bis-TMP-formaldehyde acetal, the remainder (high boilers and medium boilers) being 2%) is pumped to the 8th tray of a 10-tray bubble cap column (V=300 ml) (feed 150 ml/h), which is operated at a top pressure of 32 mbar and a bottom temperature of 194° C. The bottom discharge is heated by means of a forced-circulation evaporator (reaction volume=150 ml), from which 62 g/h of TMP formates are pumped continuously. The condensate (87 g) has two phases; distillate composition: water (55%), formaldehyde (5.2%), triethylamine (36.5%) and medium boilers (3.3%).

Composition of bottom product: TMP (29%), TMP monoformate (30%), TMP diformate (25%), TMP triformate (5%), high boilers (11%) and di-TMP and di-TMP formates, formaldehyde bis(TMP) acetal and formaldehyde-bis(TMP) acetal formates.

EXAMPLE 20

A mixture of TMP, TMP monoformate, TMP diformate and TMP triformate (37/42/19/2), together with 1% by weight of sodium methylate, is pumped (133 ml/h) to the 6th tray of a 10-tray bubble cap column (V=360 ml). 111 ml/h of methanol are metered in continuously via the bottom flask (reaction volume=360 ml). 180 ml/h of reaction mixture are removed from the bottom by means of a pump, and 53 ml/h of distillate are obtained at the top of the column. The composition of the discharges are listed in Table 4. Examples 21 and 22 were carried out similarly.

EXAMPLES 23 AND 25

The procedure is in principle as in Example 20, except that triethylamine is added instead of sodium methylate. Table 4 shows the working conditions and results.

EXAMPLE 26

176 g of the bottom discharge from Example 19 are stirred with 300 g of methanol and 9 g of triethylamine in a 1 l stirred flask for 30 minutes at 40° C. Thereafter, first methyl formate and then methanol and triethylamine are distilled off via a short column. The following fractions are then obtained in the same apparatus at a reduced pressure of 2 mbar:

| I   | bp. 120–136° C. | 4 g   | 80% of TMP (GC) |
|-----|-----------------|-------|-----------------|
| II  | bp. 140–160° C. | 124 g | 99.3% of TMP (GC) |
| III | bp. 218–225° C. | 20 g  | 14% of TMP, 86% of di-TMP and TMP FA TMP |
| IV  | Residue         | 2 g   |                 |

Fraction II has an OH number of 1232. The yield of TMP with respect to n-butyraldehyde is 87.8% over all reaction stages (Example 1, Example 10, Example 19).

EXAMPLE 27

2167 g of crude discharge from Example 1 are dewatered by means of a falling-film evaporator as in Example 10 and separated off together with excess formaldehyde and excess triethylamine. Distillate: 1390 g, bottom product: 774 g.

In a 1 l flask, the above 774 g of bottom product are heated and low boilers are distilled off via a Vigreux column. The temperature is increased from 140° C. to 180° C. Finally, reduced pressure of 300 mbar is applied. Distillate: 411 g, bottom product: 351 g.

238 g of methanol and 1.8 g of sodium methylate are added to the resulting formate mixture (351 g) in the same apparatus, and 295 g of a mixture of methyl formate and methanol are distilled off at atmospheric pressure. A subsequently performed distillation gives the following fractions:

| I   | bp.$_4$ 110–125° C. | 2.4 g   | 80% of TMP (GC) |
|-----|---------------------|---------|-----------------|
| II  | bp.$_4$ 148–160° C. | 227.3 g | 99.3% of TMP (GC) |
| III | Residue             | 65.4 g  |                 |

The TMP yield over all working-up stages (with respect to n-butyraldehyde) is 87.9% (91% with TMP in the residue).

EXAMPLE 28

32.4 ml of triethylamine (1.5 mol) 11.1 ml of n-propanal (1 mol) and 147 ml of formaldehyde (15% strength, 4.5 mol) are passed, per hour, into a continuously operated reaction cascade comprising three flasks connected in series and provided with a stirrer (reaction volume in each case 300 ml). The stirred flasks are heated as follows: flask 1=42° C., flask 2=60° C., flask 3=78° C.

3800 g of the discharge thus obtained are evaporated down to 1010 g in a rotary evaporator. Thereafter, the residue is gradually heated to 180° C. at atmospheric pressure and finally reduced pressure of 300 mbar is applied at this temperature. Water, formaldehyde and triethylamine are distilled off via a Vigreux column. 400 ml of methanol are added to the residue, and 40 g of triethylamine are introduced. Methyl formate, methanol and triethylamine are then distilled off. The remaining methanolic solution is concentrated until it contains 50% by weight of trimethylolethane. Trimethylolethane separates out as a result of the addition of methyl isobutyl ketone, and trimethylolbutane is separated out twice more from the mother liquor by further concentration; a total of 342 g of trimethylolethane are obtained. The yield (with respect to n-propanal) is 75%.

EXAMPLE 29

31.6 ml of triethylamine (1.5 mol) 15.5 ml of n-propanal (1 mol) and 143 ml of formaldehyde (15% strength, 4.5 mol) are passed, per hour, into a continuously operated reaction cascade comprising three flasks connected in series and provided with a stirrer (reaction volume in each case 300 ml). The stirred flasks are heated as follows: flask 1=42° C., flask 2=70° C., flask 3=78° C.

3845 g of the discharge thus obtained are evaporated down in a rotary evaporator. The residue is then heated as in Example 28, water, formaldehyde and triethylamine being distilled off via a Vigreux column. 400 ml of methanol are added to the residue, and 40 g of triethylamine are introduced. Methyl formate, methanol and triethylamine are then distilled off. The remaining solution is separated into three fractions by distillation.

| I   | Forerun            | 21 g  | 30% of trimethylolbutane (GC) |
|-----|--------------------|-------|-------------------------------|
| II  | bp.$_1$ 155–160° C. | 283 g | 98% of trimethylolbutane (GC) |
| III | bp.$_2$ 195–198° C. | 125 g | 7.4% of trimethylolbutane; 74% of formaldehyde bis(TMB)-acetal |

The yield of trimethylolbutane (TMB) with respect to n-pentanal is 58%, and the yield of formaldehyde bis(TMB)-acetal is 19%.

EXAMPLE 30

27.6 ml of triethylamine (1.5 mol) 45.2 ml of aqueous acetaldehyde (13.8% strength, 1 mol) and 115.2 ml of formaldehyde (20% strength, 5.5 mol) are passed, per hour, into a continuously operated reaction cascade comprising three flasks connected in series and provided with a stirrer (reaction volume in each case 300 ml). The stirred flasks are heated as follows: flask 1=27° C., flask 2=30° C., flask 3=40° C.

4376 g of the discharge thus obtained are evaporated down in a rotary evaporator. Thereafter, the residue is gradually heated to 180° C. at atmospheric pressure and finally reduced pressure at 300 mbar is applied at this temperature. Water, formaldehyde, triethylamine and medium boilers are distilled off via a Vigreux column. The residue is cooled to 60° C. and 400 ml of methanol are added. After the addition of 40 g of triethylamine, methyl formate, methanol and triethylamine are distilled off. Pentaerythritol is precipitated from the remaining methanolic solution and is filtered off with suction through a Büchner funnel. The mother liquor is freed from methanol, and acetone is added to it. Further pentaerythritol is obtained. A total of 283 g are obtained. The yield (with respect to acetaldehyde) is 61%.

EXAMPLE 31

31 ml of cyclohexanone (0.3 mol) and 165 ml of 30% strength formaldehyde (1.5 mol) are initially taken in a three-necked flask. 62 ml of triethylamine (0.45 mol) are added dropwise, the mixture heating up to 60° C. Stirring is carried out for a further 6 hours at this temperature. The conversion with respect to cyclohexanone is 90%. The reaction mixture is evaporated down in a rotary evaporator and then heated at 180° C. in order to distil off unconverted cyclohexanone, water, triethylamine and formaldehyde. Finally, reduced pressure of 300 mbar is applied at 180° C. The residue of 70 g is taken up in 100 ml of methanol, and 7 g of triethylamine are added. Methyl formate, methanol and triethylamine are distilled off together as a mixture. 150 ml of methanolic solution remain, from which 2,2,6,6-tetrakis(hydroxymethyl)cyclohexanol is precipitated on cooling. The remaining solution is freed from residual methanol in a rotary evaporator, and further 2,2,6,6-tetrakis(hydroxymethyl)cyclohexanol is precipitated from the residue with acetone. A total of 30 g are obtained. Yield: 61%, based on converted cyclohexanone.

The Tables below list details and results from the above Examples.

TABLE 1

Reaction of n-butyraldehyde (nBA), aqueous formaldehyde (FA) and triethylamine (TEA) in a reactor cascade comprising three flasks (K1, K2 and K3)

| | Molar ratios | | | | RT***) | Temperature*) | | | GC analysis (% by weight)**) | | |
|---|---|---|---|---|---|---|---|---|---|---|---|
| Ex | FA | nBA | TEA | H₂O | (h) | K1 | K2 | K3 | TMP | DiTMP | TMP/FA/TMP |
| 1 | 4.5 | 1 | 1.5 | 42.5 | 5 | 42 | 60 | 78 | 89.2 | 6.5 | 3 |
| 2 | 4.5 | 1 | 1.5 | 42.5 | 4 | 42 | 60 | 78 | 85.5 | not determined | 3 |
| 3 | 4.5 | 1 | 1.5 | 42.5 | 3 | 42 | 60 | 78 | 82 | not determined | 3 |
| 4 | 3.5 | 1 | 2 | 33 | 5 | 42 | 60 | 78 | 81.5 | not determined | 3 |
| 5 | 4 | 1 | 1.5 | 26.6 | 5 | 42 | 60 | 78 | 83 | 7.5 | 2 |
| 6 | 5 | 1 | 1.5 | 26.6 | 5 | 42 | 60 | 78 | 83 | 5 | 5.6 |
| 7 | 6 | 1 | 2.5 | 26.6 | 5 | 42 | 60 | 78 | 83 | 2.3 | 6.2 |
| 8 | 6 | 1 | 1.5 | 52 | 5 | 42 | 60 | 78 | 90 | 4 | 5 |
| 9 | 4 | 1 | 2 | 37.7 | 5 | 42 | 60 | 78 | 85 | 8.4 | 3.8 |

*)Particular temperature (° C.) in flasks 1–3
**)GC determination after silylation of the discharges with N-methyl-N-trimethylsilyltrifluoroacetamide with internal standard
TMP/FA/TMP: Formaldehyde bis(TMP)-acetal
Di-TMP: Dimeric ethers of TMP
TMP: Trimethylolpropane
***)Residence time in hours

TABLE 2

Removal of low boilers (triethylamine, water, formaldehyde) in a falling-film evaporator at atmospheric pressure

| Ex. | Temp. (° C.) | Feed (ml/h) | Distillate (g/h) | Bottom product (g/h) | HCOOH*) (%) | H₂O**) (%) |
|---|---|---|---|---|---|---|
| 10 | 150 | 120 | 80 | 43 | 13.5 | 12 |
| 11 | 130 | 250 | 83 | 167 | 8.4 | 52 |
| 12 | 150 | 250***) | 114 | 140 | 13.8 | 20 |
| 13 | 180 | 120 | 88 | 33 | 12.8 | 13 |
| 14 | 170 | 90 | 65 | 25 | 12.2 | 14 |

*)Titrimetric determination
**)Titrimetric determination (according to Karl Fischer)
***)Feed is bottom product from Example 11

TABLE 3

Esterification of crude TMP discharges in a
10-tray bubble cap column
Feed to 8th tray, heating by forced-circulation evaporator

| Ex. | Temperature (°C.) Bottom | Tray 3 | Tray 5 | Top | Pressure (mbar) | Feed (ml/h) | Bottom product (ml/h) | HCOOH conver sion* |
|---|---|---|---|---|---|---|---|---|
| 15 | 193 | 178 | 78 | 39 | 63 | 214 | 100 | 98.8 |
| 16 | 188 | 155 | 48 | 44 | 114 | 214 | 100 | 97 |
| 17 | 193 | 178 | 52 | 38 | 63 | 120 | 52 | 98.7 |
| 18 | 196 | 191 | 110 | 35 | 35 | 150 | 66 | 99.5 |
| 19**) | 194 | 180 | 112 | 32 | 32 | 150 | 62 | 99.5 |

*)Titrimetric determination
**)Feed from bottom product (Example 10)

TABLE 4

Bubble cap column (10 trays)
Volume: Column (360 ml) + flask (340 ml) = 700 ml
Feed 1: Mixture of TMP (37%), TMP monoformate (42%), TMP diformate (19%) and TMP triformate (2%)
$H_2O$ = 0.09%
HCOOH = 0.1%

| | | Example 20 | Example 21 | Example 22 | Example 23 | Example 24 | Example 25 |
|---|---|---|---|---|---|---|---|
| Feed 1 | ml/h | 145 | 133 | 170 | 160 | 255 | 141 |
| TMP/TMP | g/h | 162 | 153 | 196 | 184 | 292 | 162 |
| formates | mol/h | 1 | 0.94 | 1.2 | 1.14 | 1.8 | 1 |
| | above tray | 10 | 6 | 6 | 10 | 10 | 10 |
| Catalyst | | NaOMe | NaOMe | NaOMe | NEt3**) | — | — |
| Amount | % by weight | 1% | 0.25% | 0.125% | 5% | | |
| Feed 2 | ml/h | 161 | 111 | 74 | 133 | — | — |
| MeOH | g/h | 128 | 88 | 58 | 105 | — | — |
| | mol/h | 4 | 2.7 | 1.8 | 3.28 | — | — |
| | above tray | bottom | bottom | bottom | bottom | — | — |
| Feed 2a | ml/h | — | — | — | — | 129 | 88 |
| MeOH/NEt3/$H_2O$ | g/h | — | — | — | — | 103 | 71 |
| | mol MeOH/h | — | — | — | — | 1.9 | 1.3 |
| | mol NEt3/h | — | — | — | — | 0.32 | 0.22 |
| | mol $H_2O$/h | — | — | — | — | 0.44 | 0.31 |
| | above tray | — | — | — | — | 2 | 2 |
| | MeOH/NEt3/$H_2O$ | — | | | | 60/32/8 | 60/32/8 |
| Catalyst | | — | — | — | — | NEt3 | NEt3 |
| Amount | % by weight | | | | | 22% | 22% |
| Average residence time | (h) | 2.3 | 2.3 | 2.3 | 2.4 | 1.8 | 3 |
| Temperature (°C.) | Bottom | 68 | 72 | 82 | 73 | 84.5 | 83 |
| | Tray 6 | 63 | 61 | 61 | 67 | 41 | 60 |
| | Tray 8 | 62 | 51 | 56 | 58 | 38 | 38 |
| | Tray 10 | 32 | 32 | 32 | 33 | 31 | 30 |
| | Boiling limit | 35 | 34.5 | 34.5 | 35 | 31 | 31 |
| Bottom discharge | ml/h | 235 | 180 | 195 | 230 | —a) | —b) |
| Conversion | (based on formates) | 100 | 100 | 99.6 | 99.9 | 98 | 100 |
| Distillate | (ml/h) | 60 | 53.5 | 57 | 54 | — | — |
| Composition | MeFO*) | 85.3 | 88 | 86 | 82 | 98.8 | 94.4 |
| | MeOH | 14.2 | 12 | 14 | 11 | 0.9 | 3.9 |
| | NEt3**) | — | — | — | 6 | 0.25 | 1.7 |
| | $H_2O$ | — | — | — | — | 0.05 | Spur | a) Composition (GC % by area)MeOH 5.1; NEt3 20; TMP 72.5; TMP formate 1.5
b) Composition (GC % by area)MeOH 7.1; NEt3 26; TMP 65.4; TMP formate —
*)MeFo = Methyl formate
**)NEt3 = Triethylamine

We claim:

1. A process for the preparation of a formate containing polyalcohol product by reaction of an alkanal or keton with formaldehyde in aqueous solution in the presence of a tertiary amine, wherein the reaction is carried out using a temperature gradient with increasing temperature, and for 0.5–24 hours, and 0.6–5 mol of tertiary amine, based on 1 mol of alkanal or ketone are employed, and the process is carried out without hydrogenation of the product mixture, wherein said temperature gradient with increasing temperature is effected in a three-stage reactor cascade using temperatures of 20–40° C./40–70° C./70–90.

2. A process for the preparation of a polyalcohol, which comprises the stages:
   (a) reaction of a alkanal or ketone with formaldehyde in aqueous solution in the presence of a tertiary amine, to form a formates containing polyalcohol product mixture according to claim 1,
   (b) removal of water, excess tertiary amine, excess formaldehyde, (c) heating of remaining mixture from (b) with removal of further formaldehyde and tertiary amine with formation of the formates of the polyalcohol,
(d) transfer of tertiary amine removed from stage (b) and/or from stage (c), to synthesis stage (a) and/or to the subsequent transesterification stage (e),
(e) transesterification of the resulting formates of the polyalcohol from stage (c) with an alcohol of the formula ROH in the presence of a transesterification catalyst to give polyalcohols and formates of the formula

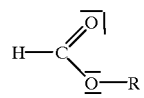

where R is a hydrocarbon radical, and
(f) isolation of the polyalcohols.

3. A process as claimed in claim 2, wherein the transesterification catalyst is a tertiary amine.

4. A process as claimed in claim 2, wherein the transesterification is carried out in the presence of a trialkylamine as a transesterification catalyst, the amount of the trialkylamine used being 0.01–75 mol %, based on 1 mol of formate of the polyalcohol formate as 100 mol %.

5. A process as claim in claim 2, wherein the material isolated from stages (c) and (b) is separated into the following mixtures in a stage (g):
 1. an alcohol/teratary amine/water mixture, at least some of which is fed to stage (e),
 2. a mixture of water and formaldehyde, at least some of which is fed to stage (a), and
 3. an aqueous solution enriched with medium boilers.

6. A process as claimed in claim 2, wherein the process is carried out without hydrogenation of the product mixture of stage (a).

7. A process as claimed in claim 1, wherein the ratio of the reactants is 0.5–10 mol of formaldehyde.

8. A process as claimed in claim 1, wherein the reaction is carried out with a two- or three-stage temperature gradient.

9. A process as claimed in claim 1, wherein the temperature is in the range of from 20 to 90° C.

10. The process of claim 1 wherein the time of reaction is 1–6 hours.

11. The process of claim 1 wherein the amount of tertiary amine is 0.8–2 moles.

12. The process of claim 5 wherein the desired polyalcohol and a mixture of alcohol and tertiary amine are obtained in stage (f) by separation and some of said mixture is recycled to stage (e), and a part of this mixture of alcohol and tertiary amine is transferred to a stage (g) in which materials isolated from stages (b) and (c) and this bleed stream from (f) is separated into the following three mixtures, preferably
 1. An alcohol/tertiary in a mixture, at least one of which is fed to stage (e),
 2. A water/tertiary amine/formaldehyde mixture, at least some of which is fed to stage (a), and
 3. An aqueous solution enriched with medium boilers.

13. The process of claim 12 wherein the desired polyalcohol and mixture of alcohol and tertiary amine obtained in stage (f) is separated by distillation and some of said mixture is recycled to stage (e), and a part of this mixture of alcohols and tertiary amine is transferred to a stage (g) in which materials isolated from stages (b) and this bleed stream from (f) are separated into the following three mixtures:
 1. an alcohol/tertiary amine mixture, at least one of which is fed to state (e),
 2. A water/tertiary amine/formaldehyde mixture, at least some of which is fed to stage (a), and
 3. an aqueous solution enriched with medium boilers.

14. The process of claim 13 wherein the separation into the three mixture, 1., 2., and 3., is carried out by distillation.

* * * * *